United States Patent [19]

Balzarini et al.

[11] Patent Number: 5,527,900
[45] Date of Patent: Jun. 18, 1996

[54] N3-ALKYL-2',5'-0-SILYLATED-3'-SPIRO-THYMIDINE DERIVATIVES

[75] Inventors: Jan M. R. Balzarini, Louvain; Erik D. A. De Clerco, Lovenjoel, both of Belgium; María-José Camarasa-Rius, Madrid, Spain; María J. Pérez-Pérez, Las Palmas, Spain; Ana San-Félix-García, Madrid, Spain

[73] Assignees: Stitching Rega VZW, Belgium; Consejo Superior de Investigaciones Instituto de Quimica Medica, Spain

[21] Appl. No.: 939,410

[22] Filed: Sep. 3, 1992

[30] Foreign Application Priority Data

Sep. 4, 1991 [EP] European Pat. Off. .............. 91202259

[51] Int. Cl.⁶ .......................... A61K 31/70; C07H 19/067
[52] U.S. Cl. ......................................................... 536/28.54
[58] Field of Search .............................. 536/28.54, 28.2; 514/50, 951, 937, 969; 424/45

[56] References Cited

FOREIGN PATENT DOCUMENTS 0382526 8/1990 European Pat. Off. .

OTHER PUBLICATIONS

Velasquez et al., J. Med. Chem. 36: 3230–3239, 1993.
"Enantiomeric synthesis of (+)-BCH-189 [(+)-. . . (2S, 5R)-1-[2-(hydroxy-methyl)-1,3-oxathiolan-5-yl]cytosine] from D-mannose and its anti-HIV activity," Chemical Abstracts, vol. 115, No. 21, pp. 1006, 1991, Abstr. No. 232751s.

Primary Examiner—Gary L. Kunz
Attorney, Agent, or Firm—Webb Ziesenheim Bruening Logsdon Orkin & Hanson

[57] ABSTRACT

Nucleoside analogs possessing anti-HIV activity and having a 3'-spiro moiety and blocking groups at the 2'- and 5'-positions. The preferred species is shown in the structure below:

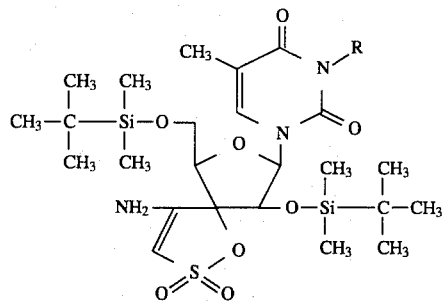

wherein R is alkyl.

4 Claims, No Drawings

N3-ALKYL-2',5'-0-SILYLATED-3'-SPIRO-THYMIDINE DERIVATIVES

The present invention relates to substituted nucleoside derivatives, as well as to their chemical synthesis and to antivirally active pharmaceutical compositions containing said compounds.

Among the most potent and selective anti-HIV (Human Immunodeficiency Virus) agents, which seem to act through inhibition of reverse transcriptase, are the 2', 3'-dideoxynucleosides. 3'-Azido-3'-deoxythymidine (AZT) and 2', 3'dideoxy-inosine have been, so far, the only approved drugs for treatment of AIDS in humans.

It is now well established that AZT prolongs the life of ARC and AIDS patients, decreases the frequency as well as severity of opportunistic infections, and partially restores the immunological competence of the patients. However, long-term treatment of AIDS patients with AZT is compounded by a number of toxic side effects, the main drawback being bone marrow suppression. Shortly after the discovery of AZT as an effective anti-retrovirus agent, various other 2', 3'-dideoxynucleoside (ddN) analogues were identified as potent and selective HIV inhibitors, and some of these ddN analogues are now subject of clinical trials.

Recently, different classes of compounds have been established to inhibit HIV-1, but not HIV-2 or SIV replication. These highly specific HIV-1 inhibitors include the 6-substituted acyclouridine derivatives, tetrahydroimidazoben-zodiazepiones and -thiones, dipyridodiazepinones, pyridinones, and bis(heteroaryl)piperazines.

After extensive research it has now been found that a selective inhibiting effect on HIV-1 is displayed by a novel class of substituted nucleoside derivatives according to claim 1.

The 50% effective concentration ($EC_5O$) of the most active of these compounds for HIV-1 ranged from 0.034 to 0.439 μg/ml. The 50% cytotoxic concentration ($CC_5O$) for MT-4 cells ranged from 2.35–>200 μg/ml.

Initial structure-activity studies revealed that the simultaneous presence of a 3'-spirosubstituent and alkylated silyl-groups at the 2' and 5' positions of the ribose results in compounds which are exquisitely inhibitory. Preferred compounds comprise derivatives of formula I wherein B is a $N^3$-alkylated thymine, the 3'-position of the ribose is substituted with a spiro-substituent and the 2'-and 5'-positions are both substituted with O-silylsubstituents optionally substituted with alkyl or phenyl. The most preferred compounds are {[1-2', 5'-bis-O-(tert-butyldimethylsilyl)-β-D-ribofuranosyl]- 3-N-methyl-thymine}-3' -spiro-5"-{4"-amino-1", 2"-oxathiole-2", 2-dioxide} with $EC_5O$=0,034 μg/ml, $CC_5O$=139 μg/ml and Selectivity Index=4088; or {1-[2', 5'-Bis-O-(tert-butyldimethylsilyl)-β-D-ribofuranosyl]-3-N-ethyl-thymine}-3'-spiro-5"-{4"-amino-1",2"-oxathiole-2", 2"-dioxide} with $EC_5O$=0,073 μg/ml, $CC_5O$=73 μg/ml and Selectivity Index=1000.

The compounds of this invention are represented by Formulas I and II:

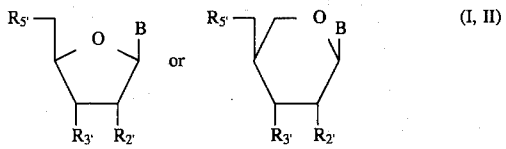

(I, II)

wherein:
B represents:

a pyrimidine of the general formula:

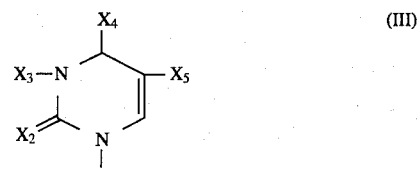

(III)

wherein:
$X_5$ is a sidechain selected from the group comprising H, alkyl, alkenyl, alkynyl, benzyl, halogen, cyano, thiocyano, —CH═CHR, hydroxymethyl, —$CH_2CH_2$-halogen, nitro, amino;
$X_4$ is a sidechain selected from the group comprising OH, SH, $NH_2$, $HNCH_3$, $N(CH_3)_2$, $NHCOCH_3$;
$X_3$ is a sidechain selected from the group comprising H, alkyl, alkenyl, alkynyl, benzyl;
$X_2$ is a sidechain selected from the group comprising O, S, Se;
or aza- and deaza derivatives thereof;
a purine of the general formula:

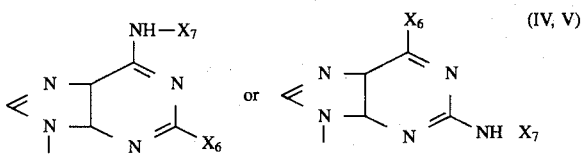

(IV, V)

wherein
$X_6$ is a sidechain selected from the group comprising H, OH, halogen, $NH_2$, $NHCH_3$, $N(CH_3)_2$;
$X_7$ is a sidechain selected from the group comprising H, alkyl, monomethoxytrityl;
or aza- and deazaderivatives thereof;
a benzimidazole of the general formula:

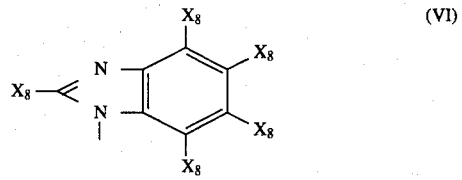

(VI)

wherein
$X_8$ are sidechains selected from the group comprising halogen, amino, alkyl, alkenyl, alkynyl, mercapto, optionally substituted;
an imidazole of the general formula:

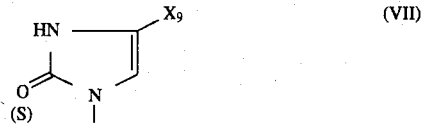

(VII)

wherein:
$X_9$ is a sidechain selected from the group comprising H, alkyl, alkenyl, alkynyl, amino, mercapto, optionally substituted,
a triazole of the general formula:

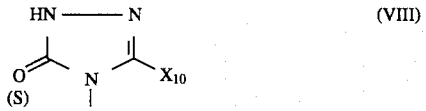

(VIII)

wherein $X_{10}$ is a sidechain selected from the group comprising H, alkyl, alkenyl, alkynyl, amino, mercapto, optionally substituted;

a sidechain of the formula

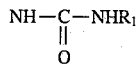

wherein $R_1$ represents a sidechain selected from the group consisting of H, ester, amino acid;

$R_3$, represents a sidechain of the formula:

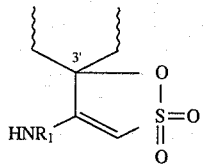

(IX)

wherein $R_1$ is a sidechain selected from the group comprising H, alkyl, alkenyl, alkynyl, optionally substituted;

or a sidechain of the general formula:

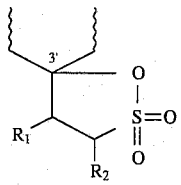

(X)

wherein $R_1$ is a side chain selected from the group comprising H, amino, hydroxyl, carboxyl, mercapto, $CH_2NH_2$, $CONH_2$, $CH_2OH$, $CH_2COOH$, $CH_2NHOH$, $CH_2SH$, alkyl, alkenyl, alkynyl, optionally substituted;

$R_2$ is a sidechain selected from the group comprising H, alkyl, alkenyl, alkynyl, amino, mercapto, optionally substituted;

or a side chain of the general formula:

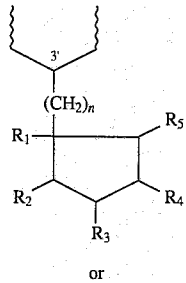

(XIII)

or

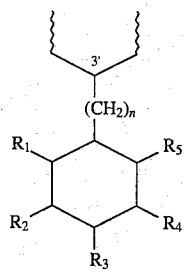

(XIV)

wherein $n \geq 0$, and the ring is either cycloalkyl or phenyl and $R_1$, $R_2$, $R_3$, $R_4$, $R_5$ are H, $NH_2$, SH, $CH_2NH_2$, $CONH_2$, COOH, $CH_2OH$, $CH_2NHOH$, $CH_2SH$, OH, optionally substituted.

or $CH_2NH_2$, $CONH_2$, $CH_2OH$, $CH_2NHOH$ or $CH_2SH$;

$R_5$, and $R_2$, are the same or different and represent a sidechain selected from the group comprising trimethylsilyl, tert-butyldimethylsilyl, tert-butyldiphenylsilyl, dimethylphenylsilyl, alkyl (optionally substituted with amino, hydroxyl, ether) aryl (optionally substituted), $(CH_2)_n$ phenyl with n=1–4; or another highly lipophylic moiety;

wherein the sugar is a pentose selected from the group consisting of ribose, arabinose, lyxose, xylose; or a hexose selected from the group consisting of glucose, mannose, galactose.

When HIV-1 strains were selected for resistance against compounds 5, 6 and 7, full resistance of these HIV-1 mutant strains against many other TSAO derivatives was noted but not against TIBO, Nevirapine and Pyridinone. The reverse transcriptase enzyme of the TSAO-resistant HIV-1 strains consistently contained a glutamic acid change at position 138 to lysine. Investigations with this mutated enzyme revealed that it completely lost affinity for TSAO, but not for other HIV-1-specific compounds (i.e. TIBO, Nevirapine, HEPT derivatives). Thus, amino acid-138 (glutamic acid) of HIV-1 RT determines the affinity of TSAO derivatives for HIV-1 RT, as well as the activity of TSAO derivatives against HIV-1 replication.

Based on these findings, it became likely that the TSAO derivatives (by their 4"-amino group of the 3'-spiro substituent) interfere with glutamic acid-138 (by its functional carboxylic acid group). The fact that, in the TSAO-resistant HIV-1 strains, glutamic acid-138 is replaced by lysine, makes it most likely that TSAO molecules containing a —COOH function in the 3'-spiro moiety may become active against TSAO-resistant HIV-1 strains. Also, these data point to the feasibility to replace the 3'-spiro moiety by another chemical entity containing —$NH_2$, —OH, or —COOH groups to keep the anti-HIV-1 activity of these compounds.

The substituted nucleoside derivatives are preferably synthesized by:

starting with a 3'-keto nucleoside of the formula:

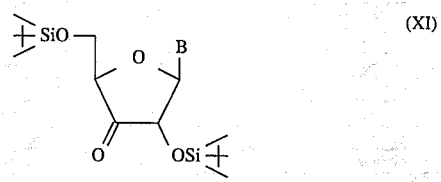

(XI)

wherein B represents a pyrimidine, purine, benzimidazole, imidazole, triazole, all of which may optionally be substituted, and O-silyl can optionally be substituted with alkyl, phenyl or other lipophillic moiety;

replacing the 3'-ketogroup therein by cyanohydrin;
converting said cyanohydrin to cyanomesylate;
converting said cyanomesylate to a spiro group; and
optionally removing one or more protecting silyl groups.

Alternatively, the nucleoside derivatives of formula I can be synthesized by:

using as a starting material a compound of formula:

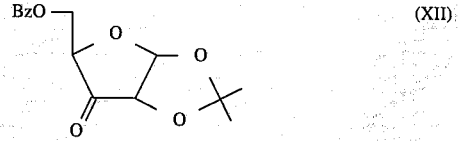

(XII)

converting the 3'-keto group therein through a cyanohydrin group to a cyanomesylate group;
converting the isopropylidene dioxy group in the 1,2-positions to two acetyloxy groups;
replacing the acetyloxy group in the 1- position by a residue of a pyrimidine or purinebase;

converting the cyanomesylate group in the 3'-position to a spiro-group;

silylating one or both hydroxyl groups in the 2' and 5' position; and optionally deprotecting one of said silylated hydroxy groups.

The invented compounds as well as their chemical synthesis and preparation of the starting materials are illustrated in the following examples, which should not be constructed however, to restrict the invention.

SYNTHESIS EXAMPLE 1

Intermediate Compounds A and B

2', 5'-Bis-O-(tert-butyldimethylsilyl)-3'-C-cyano-3'-O-mesyl-β-D-pentofuranosyl nucleosides.

A mixture of a 3'-ketonucleoside (4 mmol), water (16 mL), ethyl ether (32 mL), sodium bicarbonate (0.64 g, 8 mmol) and sodium cyanide (0.2 g, 4 mmol) was stirred vigorously at room temperature for 16 h. The organic phase was separated, and the aqueous phase was washed with ethyl ether (2×50 mL). The combined ethereal phases were dried over anhydrous sodium sulfate, filtered, and evaporated to dryness. The residue, a mixture of the two epimeric cyanohydrins, was dissolved in dry pyridine (8 mL). To this solution mesyl chloride (1.6 mL, 20 mmol) was added. The mixture was stirred at 8°–10° C. for 48 h, poured into ice and water, and extracted with chloroform (2×50 mL). The combined extracts were washed with 1N-HCl (50 mL) aqueous sodium hydrogencarbonate (50 mL), and brine (50 mL), dried over anhydrous sodium sulfate, filtered and evaporated to dryness. The residue was purified by column chromatography.

Compounds A-1 and B-1

1-[2', 5'-Bis-O-(tert-butyldimethylsilyl)-3'-C-cyano-3'-O-mesyl-β-D-xylofuranosyl]thymine and 1-[2', 5'-Bis-O-(tert-butyldimethylsilyl)-3'-C-cyano-3'-O-mesyl-β-D-ribofuranosyl]thymine.

The residue was chromatographed with ethyl acetate/hexane (1:4) as the eluent. The fastest moving bands afforded 1.18 g (53%) of A-1 a as a white foam: IR (KBr 1375, 1185 cm$^{-1}$(SO$_2$); $^1$H NMR (CDCl$_3$, 90 MHz) δ 1.96 (s, 3H, CH$_3$-5) 3.33 (s, 3H, CH$_3$SO$_2$), 4.05 (m, 2H, H-5'), 4.51 (m, 1H, H-4'), 4.87 (d, 1H, H-2', J$_{1', 2'}$=2 HZ), 6.03 (d, 1H, H-1'), 7.28 (s, 1H, H-6), 9.12 (bs, 1H, NH-3); $^{13}$C NMR (CDCl$_3$, 20 MHz) δ 12.26 (CH$_3$-5), 40.24 (CH$_3$SO$_2$), 59.17 (C-5'), 81.51, 83.55 (C-2', C-4'), 82.51 (C-3'), 91.57 (C-1'), 111.87, 112.63 (CN, C-5), 134.68 (C-6), 150.22 (C-2), 163.55 (C-4). Anal. (C$_{24}$H$_{43}$N$_3$O$_8$SSi$_2$). C, H, N, S.

The slowest moving bands afforded 0.22 g (10%) of B-1 as a white foam:

IR (KBr) 1375, 1180 cm$^{-1}$ (SO$_2$); $^1$H NMR (CDCl$_3$, 300 MHz) δ 1.94 (s, 3H, CH$_3$-5), 3.26 (s, 3H, CH$_3$SO$_2$), 4.04 (m, 2H, H-5', J$_{5'a, 5'a}$=12, J$_{4', 5'b}$=1.2, J$_{4', 5'b}$=2.1 Hz), 4.51 (d, 1H, H-2', J$_{1', 2}$=8.3 Hz), 4.73 (m, 1H, H-4'), 6.24 (d, 1H, H-1'), 7.38 (s, 1H, H-6), 8.48 (bs, 1H, NH-3); $^{13}$C NMR (CDCl$_3$, 20 MHz) δ 12.05 (CH$_3$-5), 40.33 (CH$_3$SO$_2$), 62.09 (C-5'), 80.34 (C-3'), 78.20, 84.10, 84.28 (C-2', C-1'), 112.24, 114.19 (C-5, CN), 133.68 (C-6), 150.42 (C-2), 163.18 (C-4). Anal. (C$_{24}$H$_{43}$N$_3$O$_8$SSi$_2$). C, H, N, S.

Compounds A-2 and B-2

1-[2', 5'-Bis-O-(tert-butyldimethylsilyl)-3'-C-cyano-3'-O-mesyl-β-D-xylofuranosyl]uracil and 1-[2', 5'-Bis-O-(tert-butyldimethylsilyl)-3'-C-cyano-3'-O-mesyl-β-D-ribofuranosyl]uracil.

The residue was chromatographed with ethyl acetate/hexane (1:4) as the eluent. The fastest moving bands afforded 0.26 g (11%) of B-2 as a white foam: IR (KBr 1375, 1180 cm$^{-1}$(SO$_2$); $^1$H NMR (CDCl$_3$, 90 MHz) δ 3.23 (s, 3H, CH$_3$SO$_2$) 4.03 (m, 2H, H-5'), 4.56 (d, 1H, H-2'), J$_{1', 2}$=7.5 Hz), 4.73 (m, 1H H-4'), 5.76 (dd, 1H, H-5), 6.26 (d, 1H, H-1'), 7.80 (d, 1H, H-6), 8.96 (bs, 1H, NH-3); $^{13}$C NMR (CDCl$_3$, 20 MHz) δ 40.33 (CH$_3$SO$_2$), 62.46 (C-5'), 78.76, 80.50, 84.33, 84.93 (C-2', C-3', C-4', C-1'), 103.59 (C-5), 114.00 (CN), 138.73 (C-6), 150.27 (C-2), 162.55 (C-4). Anal. (C$_{23}$H$_{41}$N$_3$O$_8$SSi$_2$). C, H, N, S.

From the slowest moving bands A-2 (1.25 g, 52%) was isolated as a white foam:

IR (KBr) 1375, 1185 cm$^{-1}$ (SO$_2$); $^1$H NMR (CDCl$_3$, 90 MHz) δ 3.20 (s, 3H, CH$_3$SO$_2$), 4.03 (m, 2H, H-5'), 4.60 (m, 1H, H-4'), 4.93 (d, 1H, H-2', J$_{1', 2}$=1.5 Hz), 5.73 (d, 1H, H-5), 5.86 (d, 1H, H-1'), 7.46 (d, 1H, H-6), 9.73 (bs, 1H, NH-3); $^{13}$C NMR (CDCl$_3$, 20 MHz) δ 40.01 (CH$_3$SO$_2$), 61.88 (C-5'), 77.71, 80.06, 82.51, 86.42 (C-2', C-3', C-4', C-1'), 105.10 (C-5) 114.33 (CN), 139.10 (C-6), 149.69 (C-2), 163.00 (C-4). Anal. (C$_{23}$H$_{41}$N$_3$O$_8$SSi$_2$). C, H, N, S.

Compounds A-3 and B-3

4-N-Acetyl-1-[2', 5'-bis-O-(tert-butyldimethylsilyl)-3'-C-cyano-3'-O-mesyl-β-D-xylofuranosyl]cytosine and 4-N-acetyl-1-[2', 5'-bis-O-(tert-butyldimethylsilyl)-3'-C-cyano-3'-O-mesyl-β-D-ribofuranosyl]cytosine.

The residue was chromoatographed with ethyl acetate/hexane (1:1) as the eluent. The fastest moving fractions afforded 1.3 g (53%) of A-3 as a white foam:

IR (KBr) 1375, 1185 cm$^{-1}$ (SO$_2$); $^1$H NMR (CDCl$_3$, 90 MHz) δ 2.28 (s, 3H, NAc), 3.17 (s, 3H, CH$_3$SO$_2$), 4.10 (m, 2H, H-5'), 4.76 (m, 1H, H-4'), 5.17 (d, 1H, H-2'), J$_{1', 2}$=1.2 Hz), 5.84 (d, 1H, H-1'), 7.50 (d, 1H, H-5), 7.82 (d, 1H, H-6), 10.6 (bs, 1H, NH-4); $^{13}$C NMR (CDCl$_3$, 20 MHz) δ 40.06 (CH$_3$SO$_2$), 59.11 (C-5'), 80.51 (C-3'), 81.57, 85.30 (C-2', C-4'), 93.29 (C-1'), 96.75 (C-5), 112.78 (CN), 143.20 (C-6), 154.87 (C-2), 163.67 (C-4), 171.45 (4NCO). Anal. (C$_{25}$H$_{44}$N$_4$O$_8$SSi$_2$). C, H, N, S.

The slowest moving fractions gave 0.37 g (15%) of B-3 as a white foam:

IR (KBr) 1375, 1180 (SO$_2$); $^1$H NMR (CDCl$_3$, 90 MHz) δ 2.30 (s, 3H, NAc), 3.24 (s, 3H, CH$_3$SO$_2$), 4.04 (m, 2H, H-5'), 4.62 (d, 1H, H-2', J$_{1', 2}$=8 Hz), 4.74 (m, 1H, H-4'), 6.42 (d, 1H, H-1'), 7.45 (d, 1H, H-5), 8.23 (d, 1H, H-6), 10.28 (bs, 1H, NH-4); $^{13}$C NMR (CDCl$_3$, 50 MHz) δ 40.36 (CH$_3$SO$_2$), 62.30 (C-5'), 80.70 (C-3'), 80.07, 84.46, 85.86 (C-1', C-2', C-4'), 97.81 (C-5), 114.10 (CN), 143.60 (C-6), 154.96 (C-2), 163.23 (C-4), 171.37 (4-NCO). Anal. (C$_{25}$H$_{44}$N$_4$O$_8$SSi$_2$). C, H, N, S.

SYNTHESIS EXAMPLE 2

General Procedure for the Synthesis of Compounds 5, 11 and 15

The {1-[2', 5'-Bis-O-(tert-butyldimethylsilyl)-β-D-pentofuranosyl]nucleosides}-3'-spiro-5"-{4"-amino-1",2"-oxathiole-2",2"-dioxide} were prepared as follows.

To a solution of the intermediate compounds 3'-C-cyano-3'-O-mesyl pentofuranosylucleoside A or B (1 mmol) in dry acetonitrile (10 mL), either Cs$_2$Co$_3$ (325 mg, 1 mmol) or DBU (0.14 mL, 1 mmol) was added. The mixture was stirred at room temperature for 1–24 h, then filtered and evaporated to dryness. The residue was purified by column chromatography.

Compound 5

{1-[2', 5'-Bis-O-(tert-butyldimethylsilyl)-β-D-ribofuranosyl]thymine}-3'-spiro-5''-{4''-amino-1'',2''-oxathiole-2'', 2''-dioxide}.

According to the general procedure, intermediate compound B-1 was treated with $Cs_2Co_3$ for 24 h. The residue was chromatographed with ethyl acetate/hexane (1:3) to give 0.11 g (85%) of compound 5 as an amorphous solid.

IR (KBr) 3400, 3320 cm$^{-1}$ ($NH_2$), 1645 (C=C—N); $^1$H NMR [$(CD_3)_2$CO, 300 MHz] δ 1.90 (s, 3H, $CH_3$-5), 4.06 (m, 2H, H-5', $J_{5'_a, 5'_b}$=12.2 Hz), 4.31 (t, 1H, H-4', $J_{4', 5}$=3.6 Hz), 4.67 (d, 1H, H-2', $J_{1', 2}$=8.0 Hz), 5.75 (s, 1H, H-3''), 6.00 (d, 1H, H-1'), 6.47 (bs, 2H, $NH_2$), 7.42 (s, 1H, H-6), 10.32 (bs, 1H, NH-3); $^{13}$C NMR [$(CD_3)_2$CO, 50 MHz] δ 63.05 (C-5'), 72.12, 85.05, 87.62 (C-2', C-4', C-3''), 92.25, 92.31 (C-1', C-3'), 112.20 (C-5), 136.22 (C-6), 151.60, 152.28 (C-2, C-4''), 163.72 (C-4). Anal. ($C_{24}H_{43}N_3O_8SSi_2$). C, H, N.

Compound 11

{1-[2', 5'-Bis-O-(tert-butyldimethylsilyl)-β-D-ribofuranosyl]uracil}-3'-spiro-5''-{4''-amino-1'', 2''-oxathiole-2'', 2''-dioxide}.

According to the general procedure, intermediate compound B-2 was treated with $Cs_2Co_3$ for 24 h. The residue was chromatographed with ethyl acetate/hexane (1:2) as the eluent to give 0.24 g (39%) of compound 11 as an amorphous solid.

IR (KBr) 3390, 3310, 3190 cm$^{-1}$ ($NH_2$, NH), 1645 (C=C—N); $^1$H NMR [$(CD_3)_2$CO, 300 MHz] δ 4.08 (m, 2H, H-5', $J_{4', 5'a}$=3.2, $J_{4', 5'b}$=2.9, $J_{5'a, 5}$=12.4 Hz), 4.35 (dd, 1H, H-4'), 4.59 (d, 1H, H-2', $J_{1', 2}$=8.1 Hz), 5.79 (s, 1H, H-3''), 5.83 (d, 1H, H-5), 6.08 (d, 1H, H-1'), 6.44 (bs, 2H, $NH_2$), 7.76 (d, 1H, H-6), 10.30 (bs, 1H, NH-3); $^{13}$C NMR [$(CD_3)_2$SO, 75 MH] δ 60.20 (C-5'), 74.50 (C-2'), 84.38, 84.58 (C-4', C-3''), 89.50 (C-1'), 92.81 (C-3'), 103.23 (C-5), 139.91 (C-6), 150.92 151.32 (C-2, C-4''), 162.73 (C-4). Anal. ($C_{23}H_{41}N_3O_8SSi_2$). C, H, N.

Compound 15

{4-N-Acetyl-1-[2', 5'-bis-O-(tert-butyldimethylsilyl)-β-D-ribofuranosyl]cytosine}-3'-spiro-5''-{4''-amino-1'',2''-oxathiole-2'',2''-dioxide}.

Intermediate compound B-3 was treated with $Cs_2CO_3$ according to the general procedure for 1 h. The residue was chromatographed with chloroform/methanol (50:1) as the eluent to give 0.14 g (70%) of compound 15 as an amorphous solid.

IR (KBr) 3410, 3320 cm$^{-1}$ ($NH_2$), 1650 (C=C—N); $^1$H NMR [$(CD_3)_2$CO, 300 MHz] δ 2.24 (s, 3H, NAc), 4.07 (m, 2H, H-5'), 4.29 (dd, 1H, H-4', $J_{4', 5'a}$=3.09, $J_{4', 5'b}$=4.66 Hz), 4.83 (d, 1H, H-2', $J_{1', 2}$=7.33 Hz), 5.71 (s, 1H, H-3''), 5.97 (d, 1H, H-1'), 6.61 (bs, 2H, $NH_2$), 7.46 (d, 1H, H-5), 8.17 (d, 1H, H-6), 9.86 (bs, 1H, NH-4); $^{13}$C NMR [$(CD_3)_2$CO, 50 MHz] δ 62.97 (C-5'), 75.94, 85.25 (C-2', C-4'), 91.12, 91.34, 91.50 (C-3', C-3'', C-1'), 97.66 (C-5), 147.13 (C-6), 152.80, 155.80 (C-2', C-4''), 164.08 (C-4), 171.64 (4-NCO). Anal. ($C_{25}H_{44}N_4O_8SSi_2$). C, H, N.

SYNTHESIS EXAMPLE 3

General Procedure for the synthesis of Intermediate compounds C, D and E

Compounds 5 and 11 can alternatively be obtained as follows. A benzoyl-isopropylidene nucleoside was treated with sodium cyanide in a two-phase ethyl ether/water system, in the presence of $NaHCO_3$, to obtain a ribocyanohydrin, which was immediately transformed in a cyanomesylate. Hyrdolysis of the 1,2-O-isopropylidene group with aqueous trifluoroacetic acid, followed by reaction with acetic anhydride-/pyridine afforded a diacetate derivative. These were glycosylated with thymine, uracil and 5-ethyluracil to obtain intermediate compounds C-1, C-2, C-3 respectively. Treatment of these intermediate compounds with $Cs_2CO_3$ gave intermediate compounds D-1, D-2 and D-3. Deprotection thereof with saturated methanolic ammonia gave fully deprotected intermediate compounds E-1, E-2 and E-3 which with reaction with tert-butyldimethylsily chloride furnished compounds 5, 11 and 10 respectively.

Compound 5

{1-[2',5'-Bis-O-(tert-butyldimethylsilyl)-β-D-ribofuranosyl-]thymine}-3'-spiro-5''-{4''-amino-1'',2''-oxathiole-2'',2''-dioxide}.

To a suspension of E-1 (0.20 g, 0.55 mmol) in dry acetonitrile (15 mL), 4-dimenthylaminopyridine (0.34 g, 2.76 mmol) and tert-butyldimethylsilyl chloride (0.414 g, 2.76 mmol), was stirred at room temperature for 24 h. The solvent was evaporated to dryness and the residue, dissolved in ethyl acetate (50 mL), was washed with cold (4° C.) 1N HCl (25 mL), water (50 mL) and brine (50 mL). The organic phase was dried over anhydrous $Na_2SO_4$, filtered and evaporated to dryness. The residue was chromatographed with chloroform/acetone (8:1) as the eluent to give 5 (0.24 g, 74%) as an amorphous solid.

Compound 11

{1-[2',5'-Bis-O-(tert-butyldimethylsilyl)-β-D-ribofuranosyl]uracil}-3'-spiro-5''-{4''-amino-1'',2''oxathiole-2'',2''-dioxide}.

To a solution of the cyanomesylate C-2 (0.98 g, 2.0 mmol) in dry acetonitrile (15 mL), $Cs_2CO_3$ (0.65 g, 20 mmol) was added. The mixture was stirred at room temperature for 6 h, then filtered, the filtrate was neutralized with acetic acid, and finally, evaporated to dryness. The residue (The spiro derivative D2) was deprotected with saturated methanolic ammonia (20 mL). After standing at room temperature overnight, the solvent was evaporated to dryness. The residue was dissolved in methanol (2 mL) and then treated with chloroform. The solid (the deprotected nucleoside E2) was filtered and suspended in dry acetonitrile (15 mL) and then, 4-dimethylaminopyridine (0.53 g, 4.4 mmol) and tert-butyldimethylsilyl chloride (0.66 g,, 4.4 mmol) were added, stirred at room temperature for 48 h, and evaporated to dryness. The residue was treated with ethyl acetate (100 mL) and water (50 mL). The organic phase was separated, and the aqueous phase was extracted with ethyl acetate (2×50 mL). The combined organics were successively washed with cold (4° C.) 1N HCl (25 mL), water (50 mL) and brine (50 mL) and, finally, dried over anhydrous $Na_2SO_4$, filtered and evaporated to dryness. The residue was chromatographed with chloroform/acetone (8:1) as the eluent to give 11 (0.28 g, 24%) as an amorphous solid.

Compound 10

{1-[2', 5'-Bis-O-(tert-butyldimethylsilyl)-β-D-ribofuranosyl]-5-ethyl-uracil}-3'-spiro-5"-{4"-amino-1",2"-oxathiole-2",2"-dioxide}.

A solution of cyanomesylate C3 (1.0 g, 1.91 mmol) in dry acetonitrile (16 mL) was treated with CsCO$_3$ (0.62 g, 1.91 mmol) for 4 h at room temperature. A similar treatment to that described for the synthesis of compound 5 afforded a residue that was chromatographed with chloroform/acetone (10:1) to give 0.37 g (32%) of compound 10 as an amorphous solid.

IR (KBr) 3500, 3420 cm$^{-1}$ (NH$_2$), 1650 (C=C—N); $^1$H NMR [(CD$_3$)$_2$SO, 200 MHz] δ 1.05 (t, 3H, C$\underline{H}_3$CH$_2$-5), 2.26 (m, 2H, CH$_3$C$\underline{H}_2$), 3.87 (m, 2H, H- 5', J$_{5'a, 5'b}$=11.4, J$_{4', 5'a}$=4.8, J$_{4', 5'b}$=7.5 Hz), 4.19 (dd, 1H, H-4'), 4.52 (d, 1H, H-2', J$_{1', 2'}$=8.4 Hz) 5.73 (s, 1H, H-3"), 5.89 (d, 1H, H-1'), 6.93 (bs, 2H, NH$_2$), 7.56 (s, 1H, H-6), 11.55 (bs, 1H, NH-3); $^{13}$C NMR [(CD$_3$)$_2$CO, 50 MHz] δ 14.17 ($\underline{C}$H$_3$CH$_2$), 21.20 (CH$_3$$\underline{C}$H$_2$), 62.99 (C-5'), 74.99 (C-2'), 85.07, 88.66 (C-4', C-3"), 91.85 (C-3'), 91.98 (C-1'), 118.20 (C-5), 136.56 (C-6), 151.55, 152.28 (C-2, C-4"), 163.23 (C-4). Anal. (C$_{25}$H$_{45}$N$_3$O$_8$SSi$_2$) C, H, N

SYNTHESIS EXAMPLE 4

Synthesis of compounds 16 and 14

Compounds 5 and 11 were reacted further so as to obtain compounds 16 and 14, respectively.

Compound 16

{1-[2', 5'-Bis-O-(tert-butyldimethylsilyl)-β-D-ribofuranosyl]-5-methyl-cytosine}-3'-spiro-5"-{4"-amino-1",2"-oxathiole-2",2"-dioxide}.

To a solution of compound 5 (0.15 g, 0.25 mmol) in dry pyridine (2 mL), a solution of 1,2,4-triazole (0.069 g, 1.01 mmol) and POCl$_3$ (0.05 mL, 0.5 mmol) in dry pyridine (5 mL) was added. The resulting solution was stirred at room temperature for 4 h, then chilled on ice, and aqueous ammonia (2 mL) was added. After stirring at room temperature for 30 min, the solvent was evaporated to dryness. The residue was treated with 20 mL of a (1:1) mixture of chloroform:methanol. The solid was filtered and the filtrate, after evaporating to dryness, was purified by column chromatography with chloroform/acetone (1:1) as the eluent to give compound 16 (0.10 g, 67%) as an amorphous solid:

IR (KBr) 3350, 3190 cm$^{-1}$ (NH$_2$), 1650 (C=C—N); $^1$H NMR [(CD$_3$)$_2$CO, 300 MHz] δ 2.05 (s, 3H, CH$_3$-5), 4.02 (dd, 1H, H-5'a, J$_{5'a, 5'b}$=11.7, J$_{4', 5'a}$=6.8 Hz), 4.09 (dd, 1H, H-5'b, J$_{4', 5}$=2.5 Hz), 4.14 H-4'), 5.09 (d, 1H, H-2', J$_{1', 2'}$=6.6 Hz), 5.51 (d, 1H, H-1'), 5.60 (s, 1H, H-3"), 6.92 (bs, 2H, NH$_2$-4"), 7.64 (s, 1H, H-6), 8.22 (bs, 2H, NH$_2$-4); $^{13}$C NMR [(CD$_3$)$_2$CO, 50 MHz]δ 13.19 (CH$_3$-5) 62.64 (C-5'), 74.38 (C-2'), 84.57, 88.98, 95.19 (C-4', C-3", C-140), 89.58 (C-3'), 104.06 (C-5), 138.42 (C-6), 154.63, 156.63 (C-2, C-4"), 167.10 (C-4). Anal. (C$_{24}$H$_{44}$N$_4$O$_7$SSi$_2$) C, H, N.

Compound 14

{1-[2', 5'-Bis-O-(tert-butyldimethylsilyl)-β-D-ribofuranosyl]-cytosine}-3'-spiro-5"-{4"-amino-1",2"-oxathiole-2",2"-dioxide}.

Compound 11 (0.18 g, 0.031 mmol) was reacted with 1,2,4-triazole (0.085 g, 1.24 mmol) and POCl$_3$ (0.06 mL, 0.62 mmol) for 4 h, and then treated with aqueous ammonia, following a similar procedure to that described for the synthesis of compound 16. The residue was chromatographed with chloroform/ethyl acetate (1:2) to yield 0.15 g (84%) of 14 as an amorphous solid;

IR (KBr) 3410, 3350, 3200 cm$^{-1}$ (NH$_2$), 1650 (C=C—N); $^1$H NMR [(CD$_3$)$_2$SO, 300 MHz] δ 3.87 (m, 2H, H-5', J$_{4', 5}$=5.3 Hz), 4.15 (t, 1H, H-4'), 4.60 (d, 1H, H-2', J$_{1', 2}$=7.8 Hz), 5.73 (s, 1H, H-3"), 5.87 (d, 1H, H-5), 5.90 (d, 1H, H-1'), 6.96 (bs, 2H, NH$_2$-4"), 7.42 (bs, 2H, NH$_2$-4), 7.74 (d, 1H, H-6). Anal (C$_{23}$H$_{42}$N$_4$O$_7$SSi$_2$) C, H, N.

SYNTHESIS EXAMPLE 5

General Procedure for the Synthesis of Compounds 6, 7, 8, 9 and 13.

(3-N-Alkyl-Nucleosides)-3'-spiro-5"-(4"-amino-1",2"-oxathiole-2",2"-dioxide).

To a solution of the spiro nucleoside 5 or 11 (1 mmol) in acetone (12 mL), K$_2$CO$_3$ (0.5 mmol) and the corresponding alkyl halide (1.1–2.0 mmol), were added. The reaction mixture was refluxed for 3–8 h. After removal of the solvent, the residue was purified by column chromatography. Other reaction parameters were as follows.

Compound 6

{1-[2', 5'-Bis-O-(tert-butyldimethylsilyl)-β-D-ribofuranosyl[-3-N-methyl-thymine}-3'-spiro-5"-{4"-amino-1",2"-oxathiole-2",2"-dioxide}

Compound 5 (0.15 g, 0.25 mmol) and methyl iodide (0.07 mL, 0.5 mmol) reacted according to the general procedure for 4 h. The residue was chromatographed with hexane/ethyl acetate (3:1) to give 6 (0.083 g, 55%) as white foam;

IR (KBr) 3390 cm$^{-1}$ (NH$_2$), 1715, 1675 (C=O), 1645 (C=C—N)); $^1$H NMR [(CD$_3$)$_2$CO, 200 MHz] δ 1.95 (s, 3H, CH$_3$-5), 3.26 (s, 3H, N—CH$_3$), 4.09 (m, 2H, H-5', J$_{gem}$=12.2, J$_{4', 5}$=3.5 Hz), 4.34 (t, 1H, H-4'), 4.66 (d, 1H, H-2', J$_{1', 2'}$=8.1 Hz), 5.76 (s, 1H, H-3"), 6.08 (d, 1H, H-1'), 6.45 (bs, 2H, NH$_2$), 7.50 (s, 1H, H-6). $^{13}$C NMR[(CD$_3$)$_2$CO, 50 MHz] 13.10 (CH$_3$-5, CH$_3$N), 63.14(C-5'), 75.43 (C-2'), 85.18, 88.27 (C-4', C-3"), 92.47 (C-1', C-3'), 111.33 (C-5), 134.47 (C-6), 152.17, 152.24 (C-2, C-4"), 163.37 (C-4). Anal. (C$_{25}$H$_{45}$N$_3$O$_8$SSi$_2$) C, H, N.

Compound 7

{1-[2', 5'-Bis-O-(tert-butyldimethylsily)-62 -D-ribofuranosyl]-3-N-ethyl-thymine}-3'-spiro-5"-{4"-amino-1", 2"-oxathiole-2",2"-dioxide}

Compound 5 (0.15 g, 0.25 mmol) and ethyl iodide (0.077 mL, 0.5 mmol) reacted, according to the general procedure, for 8 h. The residue was chromatographed with hexane/ethyl acetate (3:1) to yield 0.12 g (77%) of 7 as an amorphous solid;

IR (KBr) 3400, 3320 cm$^{-1}$ (NH$_2$), 1715, 1670 (C=O), 1645 (C=C—N)); $^1$H NMR [(CD$_3$)$_2$CO, 300 MHz] δ 1.15 (t, 3H, N—CH$_2$C$\underline{H}_3$, J=7.05 Hz), 1.94 (s, 3H, CH$_3$-5), 3.95 (q, 2H, N—C$\underline{H}_2$CH$_3$), 4.11 (m, 2H, H- 5', J$_{gem}$=12.2, J$_{4', 5'a}$=3.6, J$_{4', 5'b}$=3.5 Hz), ), 4.34 dd, 1H, H-4'), 4.66 (d, 1H, H-2', J$_{1', 2'}$=8.15 Hz), 5.77 (s, 1H, H-3"), 6.10 (d, 1H, H-1'), 6.48 (bs, 2H, NH$_2$), 7.49 (s, 1H, H-6); $^{13}$C NMR [(CD$_3$)$_2$CO, 50 MHz]δ 13.00 (CH$_3$-5), $\underline{C}$H$_3$CH$_2$N), 36.98 (CH$_3$$\underline{C}$H$_2$N), 63.14 (C-5'), 75.32 (C-2'), 85.14 (C-4'), 88.00 (C-3"), 92.52 (C-1', C-3'), 111.56 (C-5), 134.56 (C-6), 151.89, 152.20 (C-2, C-4"), 162.98 (C-4). Anal. (C$_{26}$H$_{47}$N$_3$O$_8$SSi$_2$) C, H, N.

Compound 8

{1-[2', 5'-Bis-O-(tert-butyldimethylsilyl)-β-D-ribofuranosyl]-3-N-allyl-thymine}-3'-spiro-5"{4"-amino-1", 2"-oxathiole-2", 2"-dioxide}.

Compound 5 (0.15 g, 0.25 mmol) was reacted with allyl bromide (0.023 mL, 0.27 mmol), according to the general procedure, for 3 h. The residue was chromatographed with chloroform/acetone (10:1) to afford 8 (0.10 g, 65%) as an amorphous solid;

IR (KBr) 3400, 3320 cm$^{-1}$ (NH$_2$), 1710, 1670 (C=O), 1645 (C=C—N)); $^1$H NMR [(CD$_3$)$_2$CO, 300 MHz] δ 1.96 (s, 3H, CH$_3$-5), 4.10 (m, 2H, H-5', J$_{gem}$=12.2, J$_{4', 5'a}$=3.73, J$_{4',5'b}$=3.56 Hz), 4.35 (dd, 1H, H-4'), 4.52 (d, 2H, N—CH$_2$—), 4.70 (d, 1H, H-2'), J$_{1', 2'}$=8.14 Hz), 5.12–5.25 (m, 2H, CH$_2$=CH), 5.78 (s, 1H, H-3"), 5.86 (m, 1H, CH$_2$=CH), 6.10 (d, 1H, H-1'), 6.49 (bs, 2H, NH$_2$), 7.54 (s, 1H, H-6); $^{13}$C NMR [(CD$_3$)$_2$CO, 50 MHz] δ 13.07 (CH$_3$-5), 43.88 (N—CH$_2$), 63.14 (C-5'), 75.25 (C-2'), 85.17, 88.21 (C-4', C-3"), 92.50 (C-1', C-3'), 111.52 (C-5), 118.04 (CH$_2$=CH), 132.98 (CH$_2$=CH), 134.83 (C-6), 151.78, 152.22 (C-2, C-4"), 162.87 (C-4). Anal. (C$_{27}$H$_{47}$N$_3$O$_8$SSi$_2$) C, H, N.

Compound 9

{1-[2', 5'-Bis-O-(tert-butyldimethylsilyl)-β-D-ribofuranosyl]-3-N-(3-methyl-2-butenyl)-thymine}-3'spiro-5"-{4"-amino-1", 2"-oxathiole-2", 2"-dioxide}.

According to the general procedure, compound 5 (0.15 g, 0.25 mmol) and 4-bromo-2-methyl-2butent (0.93 mL, 1.0 mmol) reacted for 2.5 h. The residue was chromatographed with chloroform/acetone (15:1) to give 9 (0.115 g, 70%) as a white solid. mp 194°–195° C. (chloroform/hexane);

IR (KBr) 3400, 3320 cm$^{-1}$ (NH$_2$), 1710, 1675 (C=O), 1645 (C=C—N)); $^1$H NMR [(CD$_3$)$_2$CO, 300 MHz] δ 1.67, 1.79 [2s, 6H, (CH$_3$)$_2$C=C], 1.94 (s, 3H, CH$_3$-5), 4.08 (m, 2H, H-5', J$_{gem}$=12.21, J$_{4', 5'a}$=3.56, J$_{4', 5'b}$=3.51 Hz), 4.34 (dd, 1H, H-4'), 4.50 (d, 2H, N—CH$_2$), 4.66 (d, 1H, H-2', J$_{1', 2}$=8.06 Hz), 5.20 (m, 1H, C=CH—CH$_2$), 5.77 (s, 1H, H-3"), 6.10 (d, 1H, H-1'), 6.48 (bs, 2H, NH$_2$), 7.49 (S, 1H, H-6); $^{13}$C NMR [(CD$_3$)$_2$CO, 50 MHz]δ 39.90 (N—CH$_2$), 63.14 (C-5'), 75.34 (C-2'), 85.14, 88.07 (C-4', C-3"), 92.54 (C-1', C-3'), 111.55 (C-5), 119.06 (C=CH), 134.60 (C-6), 137.16 [(CH$_3$)$_2$C=CH], 151.84, 152.21 (C-2, C-4"), 162.98 (C-4). Anal. (C$_{29}$H$_{51}$N$_3$O$_8$SSi$_2$) C, H, N.

Compound 13

{1-[2', 5'-Bis-O-(tert-butyldimethylsilyl)-62 -D-ribofuranosyl]-3-N-allyl-uracil}-3'-spiro-5"-{4"-amino-1", 2"-oxathiole- 2", 2"-dioxide}.

According to the general procedure, compound 11 (0.15 g, 0.26 mmol) reacted with allyl bromide (0.09 mL, 1.04 mmol), for 6 h. The residue was chromatographed with chloroform/acetone (15:1) to give compound 13 (0.143 g, 89%) as an amorphous solid;

IR (KBr) 3400, 3330 cm$^{-1}$ (NH$_2$), 1720, 1675 (C=O), 1645 (C=C—N)); $^1$H NMR [(CD$_3$)$_2$CO, 300 MHz] δ 4.07 (m, 2H, H-5', J$_{gem}$=12.45 Hz), 4.37 (dd, 1H, H-4', J$_{4, 5a}$=2.7, J$_{4', 5'b}$=3.2 Hz), 4.48 (m, 2H, N—CH$_2$), 4.59 (d, 1H, H-2', J$_{1',2}$=8.06 Hz), 5.16 (m, 2H, CH$_2$=CH), 5.80 (s, 1H, H-3"), 5.83 (m, 1H, CH$_2$=CH), 5.94 (d, 1H H-5), 6.15(d, 1H, H-1'), 6.45 (bs, 2H, NH$_2$), 7.79 (s, 1H, H-6). Anal. (C$_{26}$H$_{45}$N$_3$O$_8$SSi$_4$) C, H, N.

Pharmaceutical compositions comprising compounds of formula I as an active ingredient for treatment of AIDS and/or AIDS-related diseases in humans and animals, might take the form of suspensions, powders, solutions, sprays, emulsions, unguents or creams and can be used for topical administration, intranasal, rectal, vaginal as well as oral or parenteral (intravenous, intradermal, intramuscular, intrathecal etc.) administration. Such compositions can be prepared by combining (e.g. by mixing, dissolving etc.) of the active ingredient of formula I in the form of a free acid or salt with pharmaceutical excipients of a neutral character (such as aqueous or non-aqueous solvents, stabilizers, emulsifiers, detergents, additives) and further if necessary, with dyes and aromatizers. The concentration of the active ingredients in a pharmaceutical composition may vary widely between 0.1% to 100 %, depending on the nature of treatment and mode of administration. Further, the dose of the active ingredients to be administered may vary between 0.1 mg to 100 mg per kg bodyweight.

The anti-HIV properties of the 2', 3', 5'-substituted nucleoside derivates according to the invention are documented by the following examples which should not be read in a restricted sense.

The viruses used were moloney murine sarcoma virus (MSV), HIV-1 (strain HTLV-III$_B$, kindly provided by R. C. Gallo and M. Popovic, National Cancer Institute, Bethesda, Md.), HIV-2 (strain LAV-2(ROD)), kindly provided by L. Montagnier (Pasteur Institute, Paris, France), simian immunodeficiency virus (SIV) (strain SIV$_{MAC251}$, kindly provided by C. Bruck, RIT-Smith-Kline, Rixensart, Belgium).

The radiolabeled nucleosides [methyl-$^3$H]dThd (specific radioactivity: 40 Ci/mmol), [5-$^3$H]dUrd (specific radioactivity: 27 Ci/mmol), [5-$^3$H]dCyc (specific radioactivity: 18.2 Ci/mmol) and the radiolabeled amino acid L-[4,5-$^3$H]leucine (specific radioactivity: 52 Ci/mmol were derived from the Radiochemcial Centre (Amersham, England); [5-$^3$H]Urd (specific radioactivity: 21 Ci/mmol) and [5-$^3$H]Cyd (specific radioactivity: 21 Ci/mmol) and were obtained from Moravek Biochemicals Inc. (Brea, Calif.)

EXAMPLE 1

Anti-Retrovirus Activity of Purine and Pyrimidien Nucleoside Analogues.

In order to evaluate the inhibitory effects against retrovirus-induced cytopathogenicity in MT-4cells, said cells (5×10$^5$ cells/ml) were suspended in fresh culture medium and infected with HIV-1, HIV-2 or SIOV at 100 times the cell culture infective dose-50 (CCID$_{50}$) per ml cell suspension (1 CCID$_{50}$ being the dose infective for 50% of the cell cultures). Then, 100 μl of the infected cell suspension were transferred to microplate wells, mixed with 100 μl of the appropriate dilutions of the test compounds, and further incubated at 37° C. After 5 days, the number of viable cells was determined in a blood cell-counting chamber by trypan blue staining for both virus-infected and mock-infected cell cultures. The 50% effective concentration (EC$_{50}$) and 50% cytotoxic concentration (CC$_{50}$)were defined as the compound concentrations required to reduce by 50% the number of viable cells in the virus-infected and mock-infected cell cultures, respectively.

The toxicity of test compounds upon a 2-hr incubation period was determined by exposing MT-4 cells (3.5×10$^5$ cells/ml) to 100, 20, 4, 0.8 or 0.16 μg/ml of the test compounds for 2 hours at 37° C. Subsequently the cells were washed with culture medium. The pretreated cells were seeded in microplate wells at 70×10³ cells/200 µl-well and allowed to grow for 3 days at 37° C. Control cultures received similar concentrations of the test compounds during the whole incubation period. Then, cells were counted in a Coulter counter (Harpenden Hertz, England) and the $CC_{50}$ values were determined for each compound.

The substitutents on the test compounds as well as the results are listed in Table 1.

From the data in Table 1, it is clear that the presence of a 3'-spiro group together with substituted silyl groups at both C-2' and C-5' of the ribose are required for optimal inhibitory activity together with low cytotoxicity, thus resulting in a high selectivity Index (S.I.). It is also obvious that the presence of the silyl groups at C-2' and C-5', but not the 3'-spirosubstitutent are responsible for the cytotoxic activity of the compounds.

The compounds listed in Table 1 that are inhibitory against HIV-1 ($HTLV-III_B$), were also found to be active against the HIV-1/HE strain at the same order of magnitude. None of the test compounds listed in Table 1 proved effective against HIV-2 (strain ROD), SIV (strain $MAC_{251}$) in MT-4 cells or MSV in C3H/3T3 cells at subtoxic concentrations (data not shown). Compounds 9, 12, 14, 16, 17, were also found inactive against another HIV-2 strain (EHO).

EXAMPLE 2

Antiviral and cytotoxic activity of the test compounds upon delayed addition to HIV-1-infected MT-4 cells.

Mt-4 cells were suspended in culture medium, infected with HIV-1 and brought into microplate wells as described above. Then, 100 µl of the appropriate dilutions of the test compounds 5, 6 and 10, as well as the reference compounds AZT and TIBO were added to the HIV-1-infected MT-4 cell cultures at the time of infection (0 hr), or at 8, 16, 24, 40 or 48 hours after infection. After 5 days, the number of viable cells was determined and the $EC_{50}$ and $CC_{50}$ values for the test compounds were defined as described in example 1. Delay of addition of the test compounds by 17–24 hours resulted in a 10-fold decrease of antiviral activity for compounds 5, 6 and 10, and a 2- to 5-fold decrease in activity for AZT and TIBO (data not shown). If the addition of the compounds was delayed by 41 to 48 hours, the antiviral activity of compounds 5, 6 and 10, as well as that of AZT and TIBO, was almost totally lost. However, toxicity of compound 5 for MT-4 cells was not affected by the time that the compound had remained in contact with the cells. In fact, exposure of the MT-4 cells to the test compounds for as short as 24 hours or even 2 hours proved almost as inhibitory to MT-4 cell proliferation as a 1-, 3- or 5-day exposure period. This contrasts with AZT that becomes less cytostatic the shorter its exposure time to MT-4 cells (data not shown).

EXAMPLE 3

Inhibition of the incorporation of radiolabeled DNA, RNA or protein precursors into TCA-insoluble MT-4 cell material.

The incorporation of [methyl-³H]dThd, [5-³H]dUrd, [5-³H]dCyd, [5-³H]Urd, [5-³H]Cyd and L-[4,5-³H]leu into TCA-insoluble MT-4 cell material was measured in wells of a 96-well microtiter plate (Falcon-3072, Becton-Dickinson, New Jersey). To each well were added 10⁵ MT-4 cells, 0.25 µCi of the radiolabeled precursor and a given amount of test compound. The cells were allowed to proliferate for 20 to 24 hr at 37° C. in a humidified, $CO_2$-controlled atmosphere. At the end of this incubation period, the contents of the wells (200 µl) were brought onto 25-mm glass fiber filters (type A/E, Gelman Instrument Company, Ann Arbor, Mich.), and mounted on a Millipore 3025 sampling manifold apparatus. The filters were washed twice with 2 ml and 5 ml cold NaCl/Pi (phosphte-buffered saline), twice with 2 and 5 ml cold 10% trichloroacetic acid (TCA), twice with 5 and 7.5 ml cold 5% TCA, and twice with 1 ml cold ethanol.

The results are shown in Table 2. Most of the most active nucleoside derivatives, including the thymine (5), $N^3$-methylthymine (6), $N^3$-allylthymine (8), $N^3$-dimethylallylthymine (9), uracil (11), cytosine (14) and 5-methylcytosine (16) derivatives, that were not cytotoxic at 100 µg/ml to MT-4 cells (Table 1) did not markedly inhibit the incorporation of dThd, dUrd or dCyd into DNA, or incorporation of Urd or Cyd into RNA or incorporation of leucine into protein at a concentration of 100 µg/ml (Table 2). However, those compounds that proved inhibitory to MT-4 cell proliferation (i.e. compounds 5, 11 and 16) were equally inhibitory to the incorporation of the precursors into DNA, RNA or protein (Table 2). Thus, neither the thymine (5) nor the uracil (11) or 5methylcytosine (16) derivative showed preferential inhibition of the incorporation of the precursors (dThd, dUrd, dCyd, Urd, Cyd, leu) over the others.

EXAMPLE 4

Determination of the partition coefficient ($P_a$)

Partition of the test compounds between 1-octanol (Merck, Darmstadt, Germany) and 10 mM potassium phosphate buffer, pH, 7.5 (Merck), was measured as described in Balzarini et al., Biochem, Biophys. Res. Commun. 158: 413–422 (1989). Briefly, a 50 µM concentration of the test compound in potassium phosphate buffer was thoroughly mixed with an equal volume of 1-octanol for 30 min at room temperature. Then, the mixture was further equilibrated at room temperature and UV absorption was measured for the aqueous and alcoholic liquid phases. The partition coefficient ($P_a$) was calculated as the ratio of the compound concentration present in the 1-octanol phase to the compound concentration present in the aqueous phase.

Thus the partition coefficients ($P_a$) were determined for a number of test compounds listed in Table 1. 3'-Azido-2',3'-dideoxythymidine (AZT) was included for comparative purpose. The $P_a$ values for AZT and compound 1 were 1.12 and 0.117, respectively. Compounds 2, 3, 4, 5, 6, 7, 8, 11, 14, 15 were found to be present in the n-octanol phase by more than 95% compared to the aqueous phase. Consequently, the $P_a$ values could not be accurately determined but were invariably higher than 20.

The high $P_a$ values of the nucleoside anologues suggest that they might easily cross the blood-brain barrier, a property that should be beneficial in the light of the observations that HIV has marked tropism for the central nervous system.

Due to their lipophilic nature, the test compounds most likely also penetrate into the cells by passive diffusion, rather than by a facilitated transport carrier mechanism.

TABLE 1

Inhibitory effect against HIV-1 of various nucleoside-derivatives of the invention.

| Compound no. | B | $X_3$ | $X_4$ | $X_5$ | $X_6$ | $R_5'$ | $R_2'$ | $R_3'$ | EC50 | CC50 (μl/ml) | S.I. (μl/ml) |
|---|---|---|---|---|---|---|---|---|---|---|---|
| 1 | T | — | OH | CH3 | — | OH | OH | Spiro | >100 | >100 | — |
| 2 | T | — | OH | CH3 | — | OH | OSi⊰ | Spiro | >40 | 106 | <2,5 |
| 3 | T | — | OH | CH3 | — | OSi⊰ | OH | Spiro | >20 | 45 | <2 |
| 4 | T | — | OH | CH3 | — | OBZ | OSi⊰ | Spiro | >8 | 20 | <2,5 |
| 5 | T | — | OH | CH3 | — | OSi⊰ | OSi⊰ | Spiro | 0,034 | 7,7 | 227 |
| 6 | 3-Me—T | Meth. | OH | CH3 | — | OSi⊰ | OSi⊰ | Spiro | 0,034 | 139 | 4088 |
| 7 | 3-Et—T | Eth. | OH | CH3 | — | OSi⊰ | OSi⊰ | Spiro | 0,073 | 73 | 1000 |
| 8 | 3-All—T | All. | OH | CH3 | — | OSi⊰ | OSi⊰ | Spiro | 0,141 | >200 | >1418 |
| 9 | 3-DMAll—T | DiMAll. | OH | CH3 | — | OSi⊰ | OSi⊰ | Spiro | 0,239 | 73 | 252 |
| 10 | 5-Et—U | — | OH | C2H5 | — | OSi⊰ | OSi⊰ | Spiro | 0,038 | 3,2 | 82 |
| 11 | U | — | OH | H | — | OSi⊰ | OSi⊰ | Spiro | 0,114 | 8,3 | 73 |
| 12 | 5-Br—U | — | OH | Br | — | OSi⊰ | OSi⊰ | Spiro | 0,206 | 2,35 | 11 |
| 13 | 3-All—U | All. | OH | H | — | OSi⊰ | OSi⊰ | Spiro | 0,364 | 5,31 | 15 |
| 14 | C | — | NH2 | H | — | OSi⊰ | OSi⊰ | Spiro | 0,439 | ≧200 | ≧456 |
| 15 | C | — | NHOAc | H | — | OSi⊰ | OSi⊰ | Spiro | 0,097 | 7,5 | 77 |
| 16 | 5-Me—C | — | NH2 | CH3 | — | OSi⊰ | OSi⊰ | Spiro | 0,072 | 17,7 | 246 |
| 17 | A | — | — | — | NH2 | OSi⊰ | OSi⊰ | Spiro | 0,162 | 7,3 | 45 |

S.I. = Selectivity Index

TABLE 2

Inhibitory effects of substituted nucleoside dervatives according to the present invention on the incorporation of [methyl-$^3$H]dThd, [5-$^3$H]dUrd, [5-$^3$H]dCyd, [5-$^3$H]Urd, [5-$^3$H]Cyd and L-[4,5-$^3$H]leucine into MT-4 cell DNA, RNA or protein synthesis, respectively.

| | $IC_{50}{}^a$ (μg/ml) | | | | | |
|---|---|---|---|---|---|---|
| Compound | [methyl-$^3$H]dThd | [5-$^3$H]dUrd | [5-$^3$H]dCyd | [5-$^3$H]Urd | [5-$^3$H]Cyd | L-[4,5-$^3$H]leucine |
| 5 | 13 | 9.1 | 115 | 11 | 8.0 | 11.6 |
| 6 | >100 | >100 | >100 | >100 | >100 | >100 |

TABLE 2-continued

Inhibitory effects of substituted nucleoside dervatives according to the present invention on the incorporation of [methyl-³H]dThd, [5-³H]dUrd, [5-³H]dCyd, [5-³H]Urd, [5-³H]Cyd and L-[4,5-³H]leucine into MT-4 cell DNA, RNA or protein synthesis, respectively.

| Compound | $IC_{50}^{a}$ (µg/ml) | | | | | |
|---|---|---|---|---|---|---|
| | [methyl-³H]dThd | [5-³H]dUrd | [5-³H]dCyd | [5-³H]Urd | [5-³H]Cyd | L-[4,5-³H]leucine |
| 8 | >100 | >100 | >100 | >100 | >100 | >100 |
| 9 | >100 | >100 | >100 | >100 | >100 | >100 |
| 11 | 38 | 12 | 18 | 11 | 11 | 14 |
| 14 | >100 | >100 | >100 | >100 | >100 | >100 |
| 16 | 14 | 9.9 | 14 | 8.9 | 11 | 13 |

¹50% Inhibitory concentration or compound concentration required to inhibit incorporation of radiolabeled precursor.

We claim:

1. A compound selected from the group consisting of the compounds graphically represented in formulas I and II,

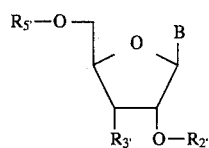

(I)

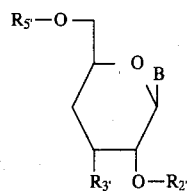

(II)

wherein B is a base selected from the group consisting of the formulas III, IV, V, VI, VII and VIII,

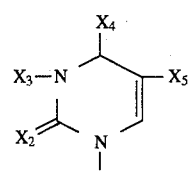

(III)

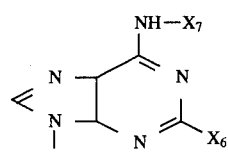

(IV)

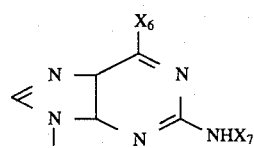

(V)

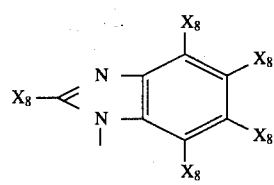

(VI)

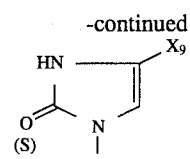

(VII)

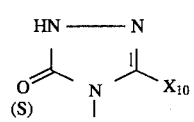

(VIII)

wherein $X_2$ is selected from the group consisting of O, S and Se;

wherein $X_3$ is selected from the group consisting of hydrogen, alkyl, alkenyl, alkynyl and benzyl;

wherein $X_4$ is selected from the group consisting of OH, SH, $NH_2$, $NHCH_3$, $N(CH_3)_2$, and $NHCOCH_3$;

wherein $X_5$ is selected from the group consisting of hydrogen, alkyl, alkenyl, alkynyl, benzyl, halogen, cyano, thiocyano, hydroxymethyl, —$CH_2CH_2$-halogen, nitro and amino;

wherein $X_6$ is selected from the group consisting of H, OH, halogen, $NH_2$, $NHCH_3$, and $N(CH_3)_2$;

wherein $X_7$ is selected from the group consisting of hydrogen, alkyl and monomethoxytrityl;

wherein $X_8$ is selected from the group consisting of halogen, amino, alkyl, alkenyl, alkynyl and mercapto;

wherein $X_9$ is selected from the group consisting of hydrogen, alkyl, alkenyl, alkynyl, amino and mercapto;

wherein $X_{10}$ is selected from the group consisting of hydrogen, alkyl, alkenyl, alkynyl, amino and mercapto;

further wherein $R_3$, for formulas III–VIII is selected from the group consisting of formulas IX and X;

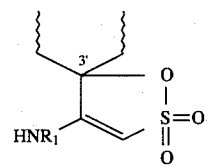

(IX)

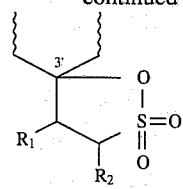

(X)

wherein when $R_3$, has formula IX, $R_1$ is selected from the group consisting of hydrogen, alkyl, alkenyl and alkynyl;

wherein when $R_3$, has formula X, $R_1$ is selected form the group consisting of hydrogen, amino, hydroxyl, carboxyl, mercapto, $CH_2NH_2$, $CONH_2$, $CH_2OH$, $CH_2NHOH$, $CH_2SH$, alkyl, alkenyl and alkynyl and $R_2$ is selected from the group consisting of hydrogen, alkyl, alkenyl, alkynyl, amino and mercapto;

and wherein $R_5$, and $R_2$, are selected from the group consisting of trimethylsilyl, tert-butyldimethylsilyl, tert-butyldiphenylsilyl, dimethylphenylsilyl, alkyl, aryl, and $(CH_2)_n$-phenyl with n=1–4.

2. The compound of claim 1 wherein said compound is an $N^3$-alkylated 2', 5'-O-silylated-3'-spiro-5''-[4''-amino-1'',2''-oxathiole-2'',2''-dioxide] thymidine.

3. The compound of claim 2 wherien said compound is {1-[2',5'-bis-O-(tert-butyldimethylsilyl)-β-D-ribofuranosyl]-3-N-methyl-thymine}-3'-spiro-5''-}4''-amino-1'',2''-oxathiole-2'',2''-dioxide} and has the formula

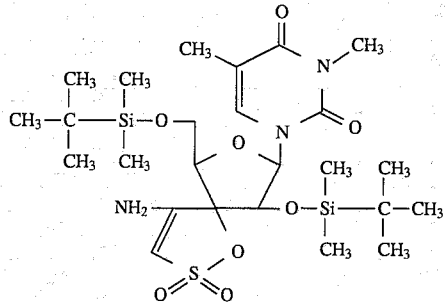

4. The compound of claim 2 wherien said compound is {1-[2', 5'-bis-O-(tert-butyldimethylsilyl)-β-D-ribofuranosyl]-3-N-ethyl-thymine}-3'-spiro-5''-{4''-amino-1'',2''-oxathiole-2'',2''-dioxide} and has the formula

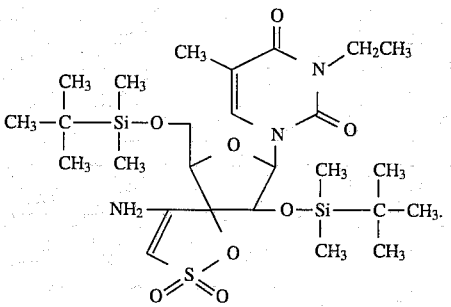

\* \* \* \* \*

UNITED STATES PATENT AND TRADEMARK OFFICE
CERTIFICATE OF CORRECTION

PATENT NO. : 5,527,900  Page 1 of 5
DATED : June 18, 1996
INVENTOR(S) : Jan M. R. Balzarini, Erik D. A. De Clercq, María-José Camarasa-Ríus, María J. Pérez-Pérez and Ana San-Félix-García It is certified that error appears in the above-indentified patent and that said Letters Patent is hereby corrected as shown below:

Title page, item '[75] Inventors:', "Louvain" should read --Leuven--.

Title page, item '[75] Inventors:', "De Clerco" should read --De Clercq--.

Title page, item '[75] Inventors:', "Camarasa-Rius" should read --Camarasa-Ríus--.

Title page, item '[56] References Cited, OTHER PUBLICATIONS', "Velasquez" should read --Velazquez--.

Title page, item '[56] References Cited, OTHER PUBLICATIONS', "pp. 1006," should read --p. 1006,--.

Column 2 Line 16 "HNCH$_3$," should read --NH$CH_3$,--.

Column 2 Line 35 "deazaderivatives" should read --deaza derivatives--.

Column 3 Line 13 "R$_3$," should read --R$_3$,--.

Column 3 Line 34 "side chain" should read --sidechain--.

Column 3 Line 41 "side chain" should read --sidechain--.

UNITED STATES PATENT AND TRADEMARK OFFICE
CERTIFICATE OF CORRECTION

PATENT NO. : 5,527,900

DATED : June 18, 1996

INVENTOR(S) : Jan M. R. Balzarini, Erik D. A. De Clercq, María-José Camarasa-Ríus, María J. Pérez-Pérez and Ana San-Félix-García It is certified that error appears in the above-indentified patent and that said Letters Patent is hereby corrected as shown below:

Column 3 Line 67 "substituted." should read --substituted;--.

Column 4 Line 2 "$R_5$, and $R_2$," should read --$R_{5'}$ and $R_{2'}$--.

Column 4 Line 66 "1- position" should read --1-position--.

Column 5 Line 43 "(KBr" should read --(KBr)--.

Column 5 Line 46 "=2 HZ)," should read --=2 Hz),--.

Column 6 Line 5 "(KBr" should read --(KBr)--.

Column 7 Line 33 "(1:2)as" should read --(1:2) as--.

Column 7 Line 38 "$J_{5'a,5'}$=" should read --$J_{5'a,5'b}$=--.

Column 7 Line 42 "75 MH]" should read --75 MHz]--.

Column 8 Line 57 "g,," should read --g,--.

Column 9 Line 11 "(32%   )" should read --(32%)--.

Column 9 Line 15 "H-  5'," should read --H-5',--.

Column 9 Line 51 "$J_{4',5'}$=2.5" should read --$J_{4',5'b}$=2.5--.

Column 9 Line 51 after "4.14" insert --(dd, 1H,--.

Column 9 Line 55 "C-140)," should read --C-1'),--.

UNITED STATES PATENT AND TRADEMARK OFFICE
CERTIFICATE OF CORRECTION

PATENT NO. : 5,527,900
DATED : June 18, 1996
INVENTOR(S) : Jan M. R. Balzarini, Erik D. A. De Clercq, María-José Camarasa-Ríus, María J. Pérez-Pérez and Ana San-Félix-García It is certified that error appears in the above-indentified patent and that said Letters Patent is hereby corrected as shown below:

Column 10 Line 28 "[2', 5'" should read --[2',5'--.

Column 10 Lines 28-29 "ribofuranosyl[" should read --ribofuranosyl]--.

Column 10 Line 49 "[2', 5'" should read --[2',5'--.

Column 10 Line 49 "62 -D" should read --ß-D--.

Column 10 Lines 50-51 "1", 2"" should read --1",2"--.

Column 10 Line 60 "H- 5',"  should read --H-5',--.

Column 10 Line 64 "(CH$_3$-5)," should read --(CH$_3$-5,--.

Column 11 Line 4 "5"{" should read --5"-{--.

Column 11 Line 4 "1", 2"" should read --1",2"--.

Column 11 Line 15 "H-2')," should read --H-2',--.

Column 11 Line 19 "(C-5')." should read --(C-5'),--.

Column 11 Line 29 "3'spiro" should read --3'-spiro--.

Column 11 Line 32 "2butent" should read --2-butene--.

Column 11 Line 41 "(s, H-3")," should read --(s, 1H, H-3"),--.

UNITED STATES PATENT AND TRADEMARK OFFICE
CERTIFICATE OF CORRECTION

PATENT NO. : 5,527,900

DATED : June 18, 1996

INVENTOR(S) : Jan M. R. Balzarini, Erik D. A. De Clercq, María-José Camarasa-Rius, María J. Pérez-Pérez and Ana San-Félix-García It is certified that error appears in the above-indentified patent and that said Letters Patent is hereby corrected as shown below:

Column 11 Line 42 "(S," should read --(s,--.

Column 11 Line 52 "62 -D" should read --ß-D--.

Column 11 Line 53 "1", 2"" should read --1",2"--.

Column 11 Line 67 "SSi$_4$)" should read --SSi$_2$)--.

Column 12 Line 34 "[5-$^3$H]dCyc" should read --[5-$^3$H]dCyd--.

Column 12 Line 37 "Radiochemcial" should read --Radiochemical--.

Column 12 Line 40 "Calif.)" should read --Ca.).--.

Column 12 Line 48 "MT-4cells," should read --MT-4 cells,--.

Column 12 Line 50 "SIOV" should read --SIV--.

Column 12 Line 60 "(CC$_{50}$)were" should read --(CC$_{50}$) were--.

Column 13 Line 34 "Mt-4" should read --MT-4--.

Column 13 Line 44 "10 -fold" should read --10-fold--.

Column 14 Line 11 "(phosphte" should read --(phosphate--.

UNITED STATES PATENT AND TRADEMARK OFFICE
CERTIFICATE OF CORRECTION

PATENT NO. : 5,527,900
DATED : June 18, 1996
INVENTOR(S) : Jan M. R. Balzarini, Erik D. A. De Clercq, María-José Camarasa-Ríus, María J. Pérez-Pérez and Ana San-Félix-García It is certified that error appears in the above-indentified patent and that said Letters Patent is hereby corrected as shown below:

Column 14 Line 27 "5methylcytosine" should read --5-methylcytosine--.

Column 17 Line 16 "$^1$50%" should read --$^a$50%--.

Claim 1 Line 57 Column 17 formula (V) "NHX$_7$" should read --NH X$_7$--.

Claim 1 Line 9 Column 19 "R$_3$," should read --R$_{3'}$--.

Claim 1 Line 13 Column 19 "R$_3$," should read --R$_{3'}$--.

Claim 1 Line 13 Column 19 "form" should read --from--.

Claim 1 Line 16 Column 19 after "CH$_2$OH," insert --CH$_2$COOH,--.

Claim 1 Line 20 Column 19 "R$_5$, and R$_2$," should read --R$_{5'}$ and R$_{2'}$--.

Signed and Sealed this

Fourteenth Day of January, 1997

Attest:

BRUCE LEHMAN

*Attesting Officer*     Commissioner of Patents and Trademarks